(12) United States Patent
Humbert et al.

(10) Patent No.: US 12,379,790 B2
(45) Date of Patent: Aug. 5, 2025

(54) SYSTEM AND METHOD FOR DETECTING HANDWRITING PROBLEMS

(71) Applicant: SOCIÉTÉ BIC, Clichy (FR)

(72) Inventors: Eric Humbert, Boulogne Billancourt (FR); Amélie Caudron, Paris (FR); Arthur Belhomme, Paris (FR); Fabrice Devige, Vanves (FR)

(73) Assignee: SOCIÉTÉ BIC, Clichy (FR)

(*) Notice: Subject to any disclaimer, the term of this patent is extended or adjusted under 35 U.S.C. 154(b) by 0 days.

(21) Appl. No.: 17/997,904

(22) PCT Filed: Apr. 30, 2021

(86) PCT No.: PCT/EP2021/061489
§ 371 (c)(1),
(2) Date: Nov. 3, 2022

(87) PCT Pub. No.: WO2021/224147
PCT Pub. Date: Nov. 11, 2021

(65) Prior Publication Data
US 2023/0148911 A1 May 18, 2023

(30) Foreign Application Priority Data
May 4, 2020 (EP) .................... 20305430

(51) Int. Cl.
*G06F 3/0354* (2013.01)
*A61B 5/00* (2006.01)
(Continued)

(52) U.S. Cl.
CPC ........ *G06F 3/03545* (2013.01); *A61B 5/0015* (2013.01); *A61B 5/1124* (2013.01);
(Continued)

(58) Field of Classification Search
CPC .. G06F 3/03545; G06F 3/0346; G06F 18/214; G06F 3/04883; A61B 5/0015;
(Continued)

(56) References Cited

U.S. PATENT DOCUMENTS 6,304,667 B1 10/2001 Reitano
6,422,775 B1 * 7/2002 Bramlett ................ B43K 29/08
382/188

(Continued)

FOREIGN PATENT DOCUMENTS

CN 108376086 A * 8/2018
WO 2015175462 A1 11/2015

OTHER PUBLICATIONS

EPO Communication issued in corresponding European Application No. 20305430.9, mailed Sep. 11, 2023.
(Continued)

*Primary Examiner* — James T Tsai
(74) *Attorney, Agent, or Firm* — Bookoff McAndrews, PLLC (57) ABSTRACT

A system for detecting handwriting problems may include a handwriting instrument including a body extending longitudinally between a first end and a second end, the first end having a writing tip which is able to write on a support, the handwriting instrument further including at least one motion sensor configured to acquire data on the handwriting of the user when a user is using the handwriting instrument, and one calculating unit communicating with the motion sensor and configured to analyze the data by an artificial intelligence trained to detect whether the user has handwriting problems.

12 Claims, 7 Drawing Sheets

(51) Int. Cl.
*A61B 5/11* (2006.01)
*G06F 3/0346* (2013.01)
*G06F 3/04883* (2022.01)
*G06F 18/214* (2023.01)
*G06V 30/228* (2022.01)
*G06V 30/32* (2022.01)

(52) U.S. Cl.
CPC .......... *A61B 5/1126* (2013.01); *A61B 5/6887* (2013.01); *A61B 5/7264* (2013.01); *A61B 5/7267* (2013.01); *G06F 3/0346* (2013.01); *G06F 18/214* (2023.01); *G06V 30/228* (2022.01); *G06V 30/347* (2022.01); *G06V 30/373* (2022.01); *A61B 2562/0219* (2013.01); *G06F 3/04883* (2013.01)

(58) Field of Classification Search
CPC ... A61B 5/1124; A61B 5/1126; A61B 5/6887; A61B 5/7264; A61B 5/7267; A61B 2562/0219; A61B 5/1122; A61B 2560/0209; A61B 2560/0214; A61B 5/002; A61B 2562/0247; A61B 2562/0257; A61B 5/1114; A61B 5/1125; G06V 30/228; G06V 30/347; G06V 30/373; G16H 50/20
See application file for complete search history.

(56) References Cited

U.S. PATENT DOCUMENTS

| | | | |
|---|---|---|---|
| 6,454,482 B1* | 9/2002 | Silverbrook | B42C 9/0081 346/140.1 |
| 6,697,524 B1* | 2/2004 | Arai | G06V 30/242 382/187 |
| 10,248,652 B1 | 4/2019 | Venkataraman et al. | |
| 11,464,443 B2 | 10/2022 | Tsoi et al. | |
| 2002/0181744 A1* | 12/2002 | Vablais | G06V 10/17 382/107 |
| 2009/0058820 A1* | 3/2009 | Hinckley | G06V 30/1456 345/173 |
| 2012/0331546 A1 | 12/2012 | Falkenburg et al. | |
| 2013/0060124 A1 | 3/2013 | Zietsma | |
| 2015/0029164 A1 | 1/2015 | Liu | |
| 2016/0259436 A1 | 9/2016 | Nicholson et al. | |
| 2016/0364010 A1* | 12/2016 | Amma | G06V 30/228 |
| 2016/0378195 A1 | 12/2016 | Lefebvre | |
| 2018/0299976 A1 | 10/2018 | Chiewcharnpipat et al. | |
| 2019/0076078 A1* | 3/2019 | Davis | G06F 3/04883 |
| 2019/0150837 A1* | 5/2019 | Dibia | G09B 19/00 |
| 2020/0202741 A1* | 6/2020 | Zhong | B43K 23/00 |
| 2020/0250413 A1 | 8/2020 | Lu et al. | |
| 2020/0251217 A1 | 8/2020 | Cassuto et al. | |
| 2020/0356251 A1* | 11/2020 | Gobera Rubalcava | G06V 30/347 |
| 2021/0076105 A1* | 3/2021 | Parmar | H04N 21/234336 |
| 2021/0232235 A1 | 7/2021 | Regani et al. | |
| 2021/0333875 A1* | 10/2021 | Horii | G06T 7/74 |
| 2022/0147791 A1 | 5/2022 | Yao et al. | |
| 2022/0366713 A1* | 11/2022 | Humbert | G06V 30/347 |
| 2023/0126043 A1* | 4/2023 | Ferrante | A61B 5/6887 401/195 |

OTHER PUBLICATIONS

Momina Moetesum, Imran Siddiqi, Nicole Vincent, Florence Cloppet, "Assessing visual attributes of handwriting for prediction of neurological disorders—A case study on Parkinson's disease", Pattern Recognition Letters, vol. 121, 2019, pp. 19-27, ISSN 0167-8655, https://doi.org/10.1016/j.patrec.2018.04.008. (https://www.sciencedirect.com/science/article/pii/S0167865518301284).

Asselborn, Thibault, et al. "Automated human-level diagnosis of dysgraphia using a consumer tablet." NPJ digital medicine, vol. 1, No. 1, Aug. 31, 2018, pp. 1-9.

Bashir, Muzaffar. "A novel multisensoric system recording and analyzing human biometric features for biometric and biomedical applications." Dissertation, Der Universität Regensburg, Dec. 10, 2010.

International Search Report and Written Opinion issued on Oct. 19, 2021 in counterpart International Application No. PCT/EP2021/061489 (19 pages, in English).

Kumar Chellapilla, Sidd Puri, Patrice Simard. High Performance Convolutional Neural Networks for Document Processing. Tenth International Workshop on Frontiers in Handwriting Recognition, Université de Rennes 1, Oct. 2006, La Baule (France).

* cited by examiner

SYSTEM AND METHOD FOR DETECTING HANDWRITING PROBLEMS

This is a national phase application of PCT/EP2021/061489, now published as WO2021224147, which in turns claims partial priority from European patent application EP20305430.9, claims 1-7, filed on 4 May 2020, now published as EP3907587, the contents of the '430.9 application being incorporated herein by reference.

TECHNICAL FIELD

This disclosure pertains to the field of systems for detecting handwriting problems.

BACKGROUND ART

Currently, several systems or methods exist for detecting particular handwriting problems. Among these handwriting problems, one can found dyslexia, learning disabilities, difficulty in forming letters, etc.

Currently, the methods used to detect handwriting problems are based on the use of a stylus-pen with which a user is asked to write on a mobile terminal specifically dedicated to detecting handwriting problems. Such a method is for example disclosed in the document U.S. Pat. No. 6,304,667. In this document, the user writes on a mobile terminal such as an electronic tablet. The tablet comprises an embedded pressure sensor able to calculate the pressure of the stylus on the electronic tablet when the user is writing. Furthermore, the method uses a database of distorted letters with which the letters written by the user are compared. This method allows detecting handwriting problems such as dyslexia. However, the material used to detect the problem is very specific and does not allow detecting easily handwriting problems for a large number of people.

SUMMARY

One purpose of this disclosure is to improve the situation.

It is proposed a system for detecting handwriting problems comprising:
- a handwriting instrument including a body extending longitudinally between a first end and a second end, the first end having a writing tip which is able to write on a support, the handwriting instrument further including at least one motion sensor configured to acquire data on the handwriting of the user when a user is using the handwriting instrument,
- one calculating unit communicating with the motion sensor and configured to analyze the acquired data by an artificial intelligence trained to detect whether the user has handwriting problems.

This system is able to detect a handwriting problem with a regular handwriting instrument. The system disclosed herein is easy to use since no further electronic components such as a dedicated tablet and stylus are needed.

The following features may be implemented, separately or in combination one with the others:

The motion sensor and the calculating unit are embedded in a second extremity of the handwriting instrument.

The system further comprises a detection device, the detection device comprising the motion sensor and the calculation unit, the detection device being mounted on the second extremity of the handwriting instrument.

The system can then be used with any already existing handwriting instrument.

The motion sensor is embedded in the handwriting instrument, the handwriting instrument further includes a short-range radio communication interface configured to communicate raw data acquired by the motion sensor to a mobile device comprising the calculating unit via a communication interface of the mobile device.

The motion sensor comprises two three-axis accelerometers.

Therefore, the motion sensor used to detect handwriting problems does not consume a lot of power.

The handwriting instrument comprises two motion sensors being one three-axis accelerometer and one three-axis gyroscope.

It increases the precision in the acquired motion data.

In examples, the three-axis gyroscope comprises a wake-up input suited for receiving a wake-up signal from the calculating unit when a movement is detected by the three-axis accelerometer, the three-axis gyroscope being configured for switching into an active state when the wake-up signal is received.

This configuration allows to reduce the consumption of power needed by the system as a function of the implemented two motion sensors.

The system further comprises a pressure sensor embedded in the handwriting instrument such as a pen or a pencil, the calculating unit being configured to further receive data acquired by the pressure sensor.

The system is then able to detect handwriting problems on the basis of different kind of data: motion data, pressure data, etc.

The system further comprises a stroke sensor configured to acquire stroke data while the user is using the handwriting instrument, the artificial intelligence being trained with the stroke data to determine handwriting problems.

The artificial intelligence is then able to determine when the user is actually using the handwriting instrument on a support and differentiate the data corresponding to an actual use of the handwriting instrument and the data acquired while the handwriting instrument is just hold in the air. In examples, the artificial intelligence is further configured to transcribe raw data acquired by the motion sensor into handwriting characters depicted on the mobile device.

In examples, the stroke sensor is the motion sensor.

In examples, the stroke sensor is a pressure sensor, or a contact sensor, or a vibration sensor.

In examples, the system does not use another embedded sensor. The system remains compact and low-power consuming.

The herein disclosed systems may be used in a method for detecting handwriting problem, comprising:
- acquiring, by means of a handwriting instrument comprising at least one motion sensor, motion data while a user is using the handwriting instrument,
- analyzing the motion data by an artificial intelligence trained to detect a handwriting problem.

The following features may be implemented, separately or in combination one with the others:

The artificial intelligence is a neural network.

In examples, the neural network is a deep neural network.

The method further comprises a prior learning step comprising:
- acquiring a plurality of motion data from a plurality of persons using the handwriting instrument,
- labelizing the acquired data,
- using end-to-end supervised learning on the labelizing to train the neural network until it converges,
- storing the neural network.

The neural network may then be trained by means of an end-to-end classification. This improves the precision of the results.

The acquired data are classified in at least one of the following classes:
- type of grip on the handwriting instrument,
- pressure applied on the handwriting instrument,
- use of the handwriting instrument among writing, drawing or coloring,
- fluidity of writing,
- dyslexia,
- dysgraphia,
- wrong ductus.

The system as described herein can thus detect a lot of different and particular handwriting problems.

The method further comprises acquiring vibration data by a stroke sensor, the method further comprising a prior learning step comprising:
- acquiring a plurality of motion data and vibration data from a plurality of persons using the handwriting instrument,
- processing the vibration data to obtain stroke timestamps labels,
- using supervised learning on the processing to train the neural network until it converges,
- storing the neural network.

The neural network may then be trained by segmentation and classification of strokes. The size of the neural network is then smaller than the neural network trained according to the end-to-end classification.

The features extracted from the strokes timestamps comprise:
- total strokes duration,
- total in air stroke duration,
- strokes mean duration,
- strokes mean and peak velocity,
- number of pauses during use of the handwriting instrument,
- ballistic index, which corresponds to an indicator of handwriting fluency which measures smoothness of the movement defined by the ratio between the number of zero crossings in the acceleration and the number of zero crossings in the velocity,
- number of zero-crossing in the acceleration during strokes,
- number of zero-crossing in the velocity during strokes.

The classification of the features of stroke timestamps is made by a hand-crafted algorithm or a learned model.

Two approaches can then be used to extract the features.

In examples, the extracted features of the stroke timestamps and motion data are classified in at least one of the following classes:
- type of grip on the handwriting instrument,
- pressure applied on the handwriting instrument,
- use of the handwriting instrument among writing, drawing or coloring,
- fluidity of writing,
- dyslexia,
- dysgraphia,
- wrong ductus.

The neural network is further trained with a data base of letters and numbers correctly formed, a sequence of strokes and a direction of the strokes of the sequence of strokes being associated to each letter and number of the data base, and wherein, based on the motion and vibration data acquired during the use of the handwriting instrument, the neural network determines if the user is forming letters and numbers correctly.

The system is then adapted to detect a lot of different handwriting problems, with a high precision, small number of components and easy use.

BRIEF DESCRIPTION OF DRAWINGS

Other features, details and advantages will be shown in the following detailed description and on the figures, on which.

DESCRIPTION OF EMBODIMENTS

Figures and the following detailed description contain, essentially, some exact elements. They can be used to enhance understanding the disclosure.

It is now referred to FIGS. 1 to 7 illustrating embodiments of a system 1 for detecting handwriting problems. The same reference numbers are used to describe identical elements of the system.

In an embodiment, a handwriting problem which can be detected according to the present disclosure can be dyslexia, dysgraphia or a difficulty to reproduce characters.

Figure 1:
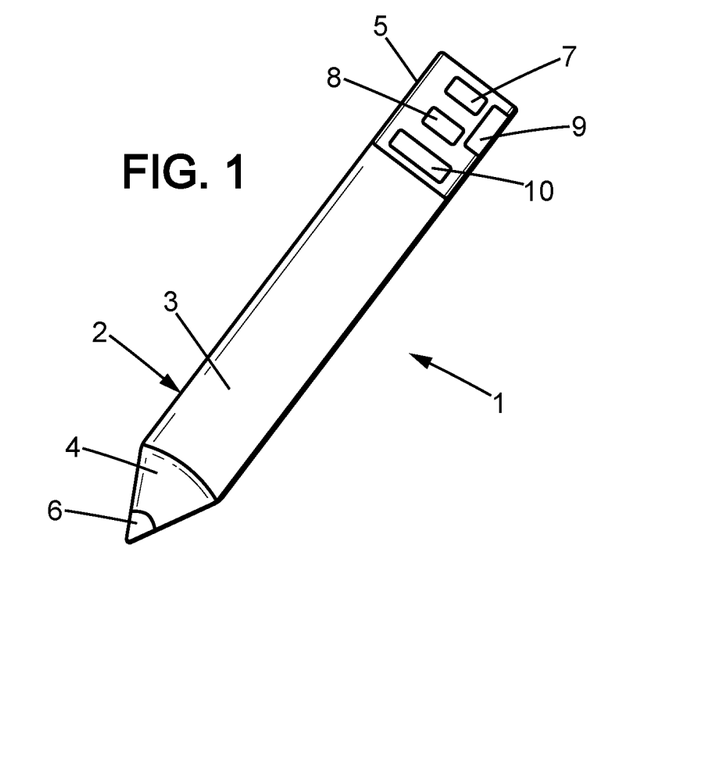
FIG. 1 shows an illustration of a system for detecting handwriting problems according to a first embodiment.
Figure 2:
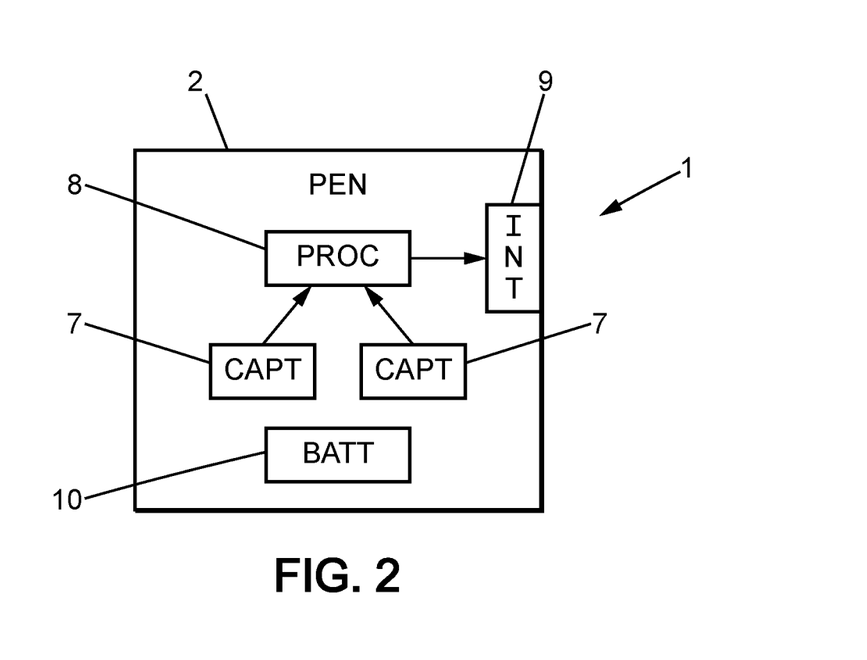
FIG. 2 shows a block schema of the system illustrated in FIG. 1.

FIGS. 1 and 2 generally illustrates a system 1 according to a first embodiment. The system 1 comprises a handwriting instrument 2. The handwriting instrument 2 may be a pen, a pencil, a brush or any element allowing a user to write or draw with it on a support. The support may be paper, canvas, or any surface on which a user can write or draw. The support may also be a coloring book. The support may be a non-electronic surface.

The handwriting instrument 2 comprises a body 3 extending longitudinally between a first end 4 and a second end 5. The first end 4 comprises a writing tip 6 which is able to write on a support. The tip 6 may deliver ink or color.

The handwriting instrument 2 further includes at least one motion sensor 7. In one embodiment, the motion sensor 7 may be a three-axis accelerometer or a three-axis gyroscope.

In the illustrated embodiments on FIGS. 1 to 7, the handwriting instrument 2 includes two motion sensors 7. In embodiments, the handwriting instrument 2 comprises two three-axis accelerometers. In embodiments, the handwriting instrument 2 comprises one three-axis accelerometer and one three-axis gyroscope.

The at least one motion sensor 7 is able to acquire data on the handwriting of the user when the user is using the handwriting instrument 2. These data are communicated to a calculating unit 8 which is configured to analyze the data and detect an eventual handwriting problem of the user. The calculating unit 8 may comprise a volatile memory to store the data acquired by the motion sensor 7 and a non-volatile memory to store a model enabling the detection of handwriting problem.

The handwriting instrument 2 may also comprise a short-range radio communication interface 9 allowing the communication of data between the motion sensor 7 and the calculating unit 8. In embodiments, the short-range radio communication interface is using a Wi-Fi, Bluetooth®, LORA®, SigFox® or NBIoT network. In embodiments, the short-range radio communication interface may also communicate using a 2G, 3G, 4G or 5G network.

The handwriting instrument 2 further includes a battery 10 providing power to at least the motion sensor 7 when the user is using the handwriting instrument. The battery 9 may also provide power to the calculating unit 8 when the calculating unit is included in the writing instrument 2.

Figure 3:
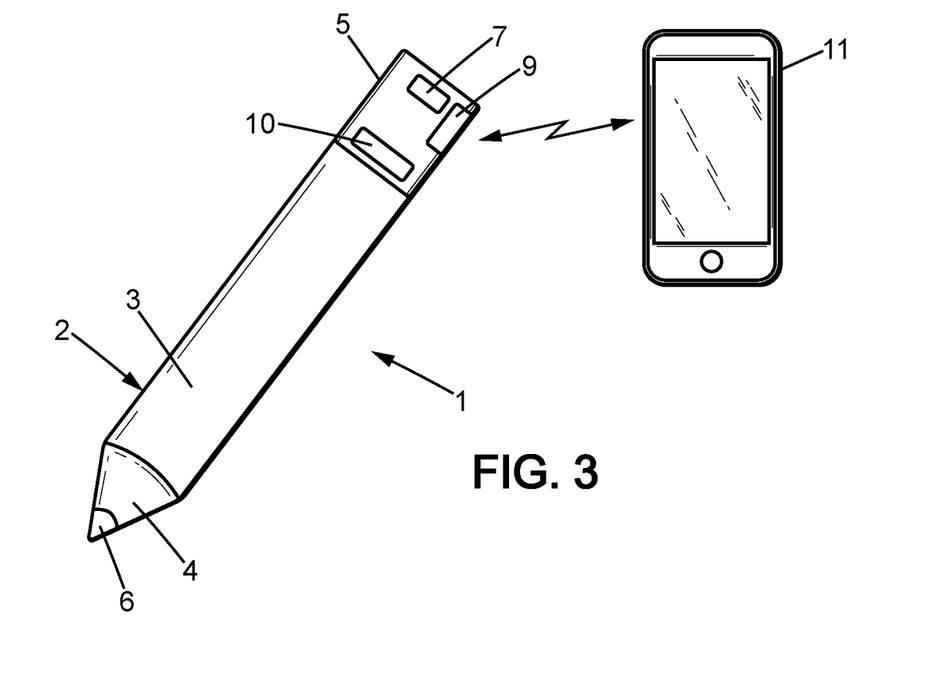
FIG. 3 shows an illustration of a system for detecting handwriting problems according to a second embodiment.
Figure 4:
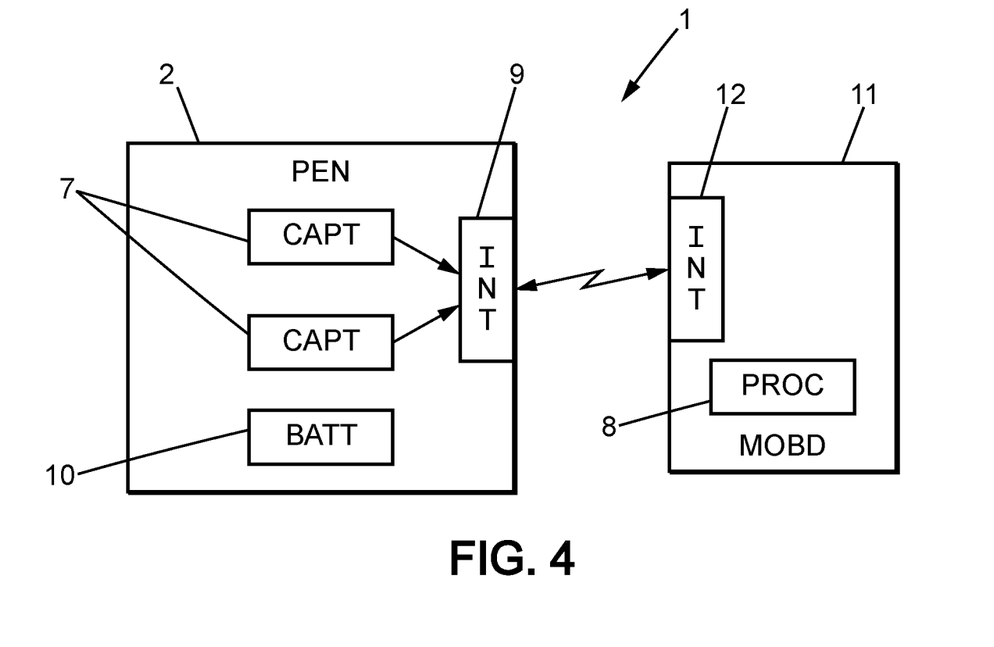
FIG. 4 shows a block schema of the system illustrated in FIG. 3.

More specifically, in the embodiment of FIGS. 3 and 4, the handwriting instrument 2 comprises the at least one motion sensor 7, the short-range radio communication interface 9 and the battery 10. The system 1 further comprises a mobile device 11, distinct from the handwriting instrument 2. The mobile device 11 may be an electronic tablet, a mobile phone or a computer. The mobile device 11 comprises the calculating unit 8. The mobile device 11 further comprises a short-range radio communication interface 12 enabling communication between the calculating unit 8 and the handwriting instrument 2.

In this embodiment, the calculating device 8 of the mobile device receives raw data acquired by the motion sensor 7 and analyzes the raw data acquired by the motion sensor 7 to detect an eventual handwriting problem.

Figure 5:
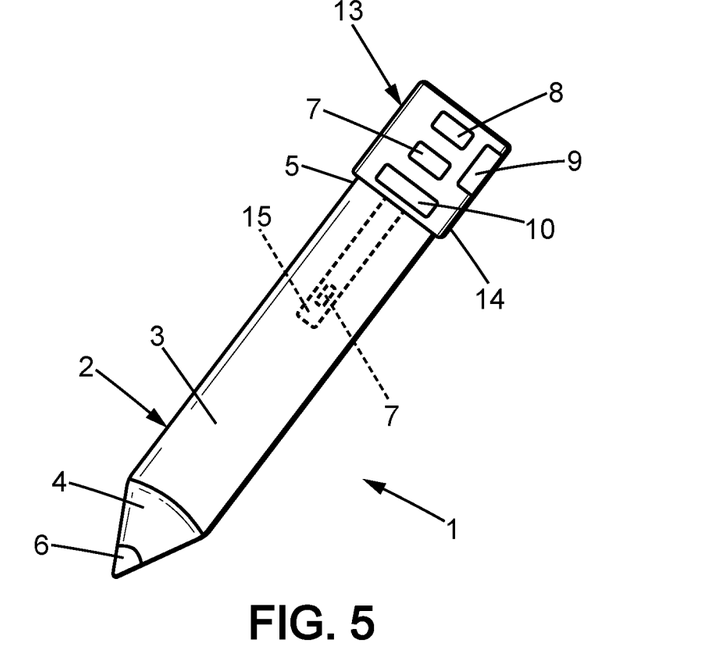
FIG. 5 shows an illustration of a system for detecting handwriting problems according to a third embodiment.
Figure 6:
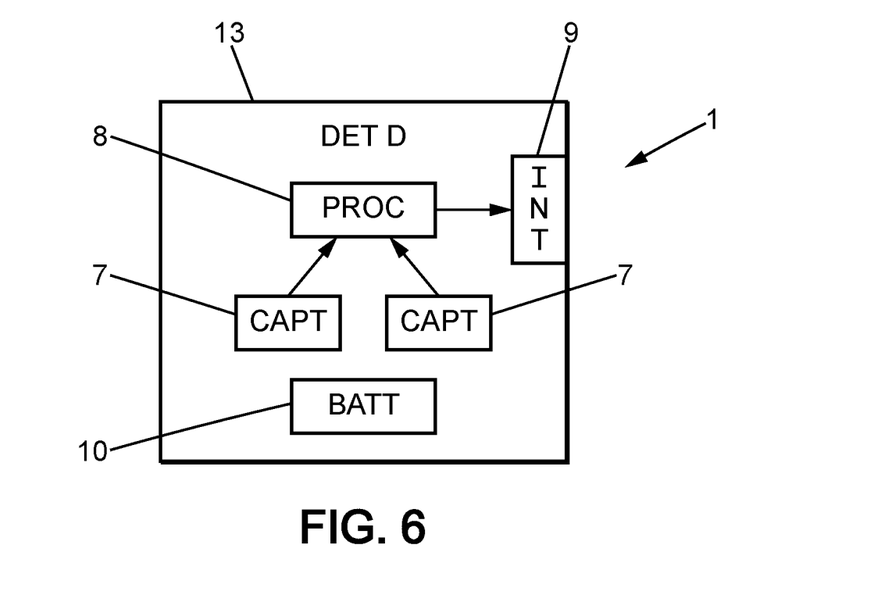
FIG. 6 shows an illustration of a system for detecting handwriting problems according to a fourth embodiment.

In the embodiment illustrated FIGS. 5 and 6, the motion sensors 7, the calculating unit 8, the short-range radio communication interface 9 and the battery 10, are not embedded in the handwriting instrument 2. In this embodiment, the electronics may be comprised in a detection device 13, distinct from the handwriting instrument 2. The detection device 13 can be mounted on the second end 5 of the handwriting instrument 2.

In this embodiment, the detection device 13 comprises a body 14 designed to be mounted on the second end 5 of the handwriting instrument 2 and a protuberant tip 15 able to be inserted in the body 3 of the handwriting instrument 2. In examples, one motion sensor 7 may be provided on the protuberant tip 15 and another motion sensor 7 may be provided in the body 14 of the detection device 13. By this means, the two motions sensors 7 are able to acquire different data during the handwriting of the user.

In embodiments, the motions sensors 7 are provided in the body 14 of the detection device 13. By this means, the detection device 13 can be mounted on any type of handwriting instrument 2, without necessitating a hollow body 3 of the handwriting instrument 2.

Figure 7:
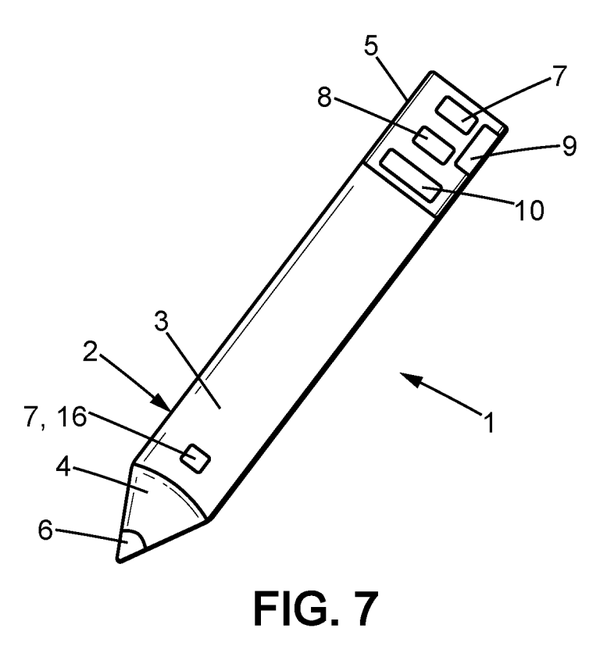
FIG. 7 shows an illustration of a system for detecting handwriting problems according to an alternative embodiment of FIGS. 1 and 2.

In the embodiment illustrated on FIG. 7, the at least one motion sensor 7, the calculating unit 8, the short-range radio communication interface 9 and the battery 10 are directly embedded in the handwriting instrument 2.

In embodiments, one motion sensor 7 may be provided close to the first end 4 of the handwriting instrument 2, while another motion sensor 7 may be provided on the second end 5 of the handwriting instrument 2.

In embodiments, the handwriting instrument 2 may also comprise a pressure sensor able to acquire data. These data can be transmitted to the calculation unit that analyze these data and the data acquired by the at least one motion sensor 7.

The pressure sensor may be embedded in the handwriting instrument 2 or in the detection device 13.

In all the embodiments described above, the calculating unit 8 receives data acquired from at least on motion sensor 7 and from the pressure sensor, if applicable, to analyze them and detect a handwriting problem.

More specifically, the calculating unit 8 may store an artificial intelligence model able to analyze the data acquired by the motion sensor 7. The artificial intelligence may comprise a trained neural network.

Figure 8:
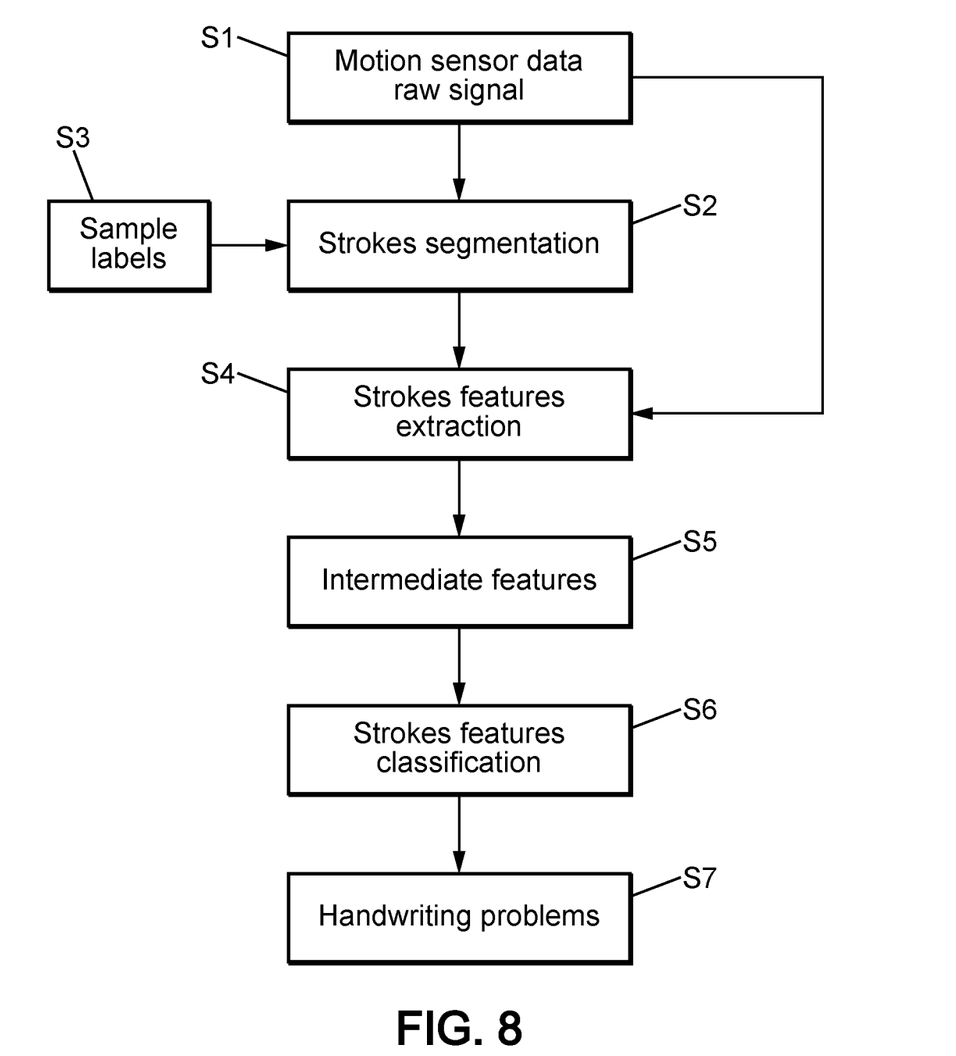
FIG. 8 shows a block diagram illustrating the training phase of the neural network in a method using the systems disclosed herein.

In the embodiment illustrated on FIG. 8, the neural network is trained according to the method of using intermediate features extraction.

More particularly, at step S1, the motion sensor 7 acquires data during the use of the handwriting instrument 2.

At step S2, the neural network receives the raw signals of the data acquired at step S1. The neural network also receives the sample labels at step S3. These labels correspond to whether or not the signal corresponds to a stroke. More precisely, the neural network is able to determine if the signal correspond to a stroke on a support. The neural network is then able to determine stroke timestamps.

More particularly, this means that the neural network is able to determine for each stroke timestamps if a stroke has actually been made on the support by the user during the use of the handwriting instrument 2.

At step S4, the calculating unit 8 performs a stroke features extraction to obtain intermediate features at step S5.

These intermediate features comprise, but are not limited to:

total strokes duration,
 total in air stroke duration,
 strokes mean duration,
 strokes mean and peak velocity,
 number of pauses during use of the handwriting instrument,
 ballistic index, which corresponds to an indicator of handwriting fluency which measures smoothness of the movement defined by the ratio between the number of zero crossings in the acceleration and the number of zero crossings in the velocity,
 number of zero-crossing in the acceleration during strokes,
 number of zero-crossing in the velocity during strokes.

From these intermediate features, the neural network is able to derive indications about handwriting problems.

At step S6, an algorithm is able to derive indications about handwriting problems.

This algorithm can be a learned model such as a second neural network, or a handcrafted algorithm.

In the embodiment where a learned model such as a neural network is used, the model is trained on a supervised classification task, where the inputs are stroke features with labels, and the outputs are handwriting problems.

In the embodiment where a hand-crafted algorithm is used, the hand-crafted algorithm can compute statistics on the stroke features and compare them to thresholds found in the scientific literatures, in order to detect handwriting problems.

Finally, at step S7, the system is able to detect handwriting problems. These handwriting problems include but are not limited to:
dyslexia,
dysgraphia,
wrong grip of the handwriting instrument,
bad character writing.

Figure 9:
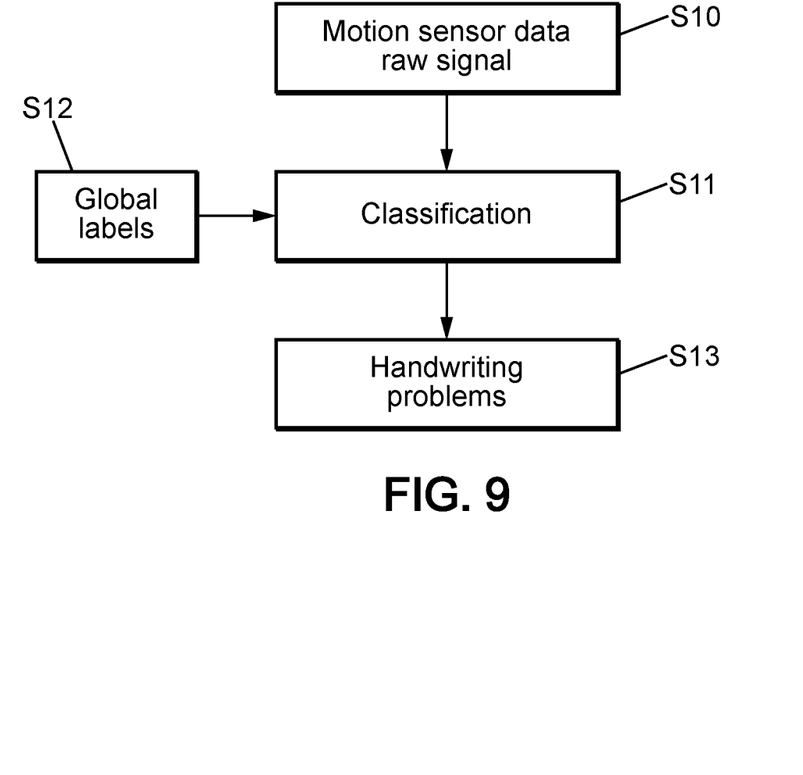
FIG. 9 shows a block diagram illustrating the training phase of the neural network in a method using the systems disclosed herein.

In the embodiment illustrated on FIG. 9, the neural network is trained according to the method of end-to-end classification.

According to this embodiment, at step S10, the data are acquired by the motion sensor 7.

The classification is made in step S11. To do learn the classification task, the neural network receives the raw signal of the data acquired by the motion sensor 7 and global labels (step S12). The global labels corresponds to the handwriting problems to be detected by the neural network which can be, but are not limited to:
dyslexia,
dysgraphia,
wrong grip of the handwriting instrument,
bad character writing.

In step S13, the neural network delivers the result.

The trained neural network described in reference with FIGS. 8 and 9 is stored.

The neural network can be stored in the calculating unit 8.

Figure 10A:
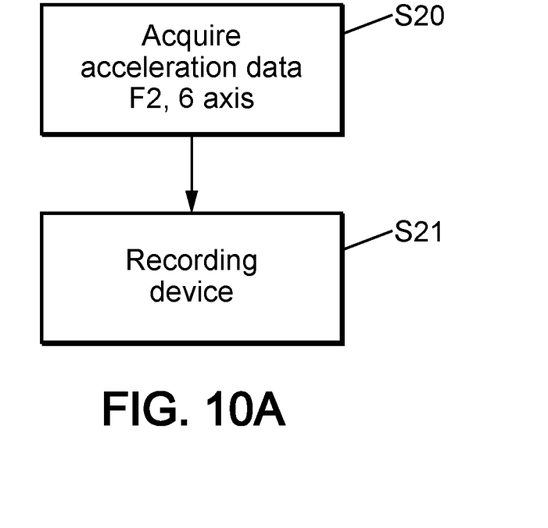
FIG. 10A to 10C illustrate block diagrams of the collect phase, training phase and inference phase of the trained neural network.

FIGS. 10A to 10O illustrate more specifically the embodiment described with reference to FIG. 8.

In order of segment the strokes (step S2 of FIG. 8), the neural network may determine the timestamps of the strokes on the support.

This information can be detected by a stroke sensor 16. The stroke sensor 16 is advantageously embedded in the handwriting instrument or in the detection device 13 mounted on the handwriting instrument.

In embodiments, the stroke sensor 16 may be a pressure sensor, a contact sensor or a vibration sensor. Then, the neural network receives the data collected by the stroke sensor 16 at step S3.

Figure 10B:
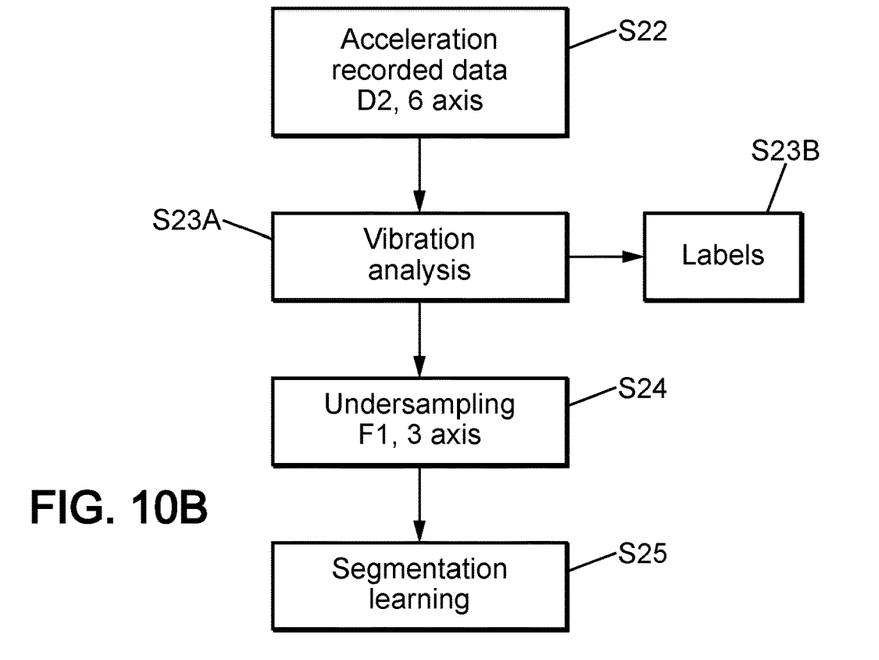
Figure 10C:
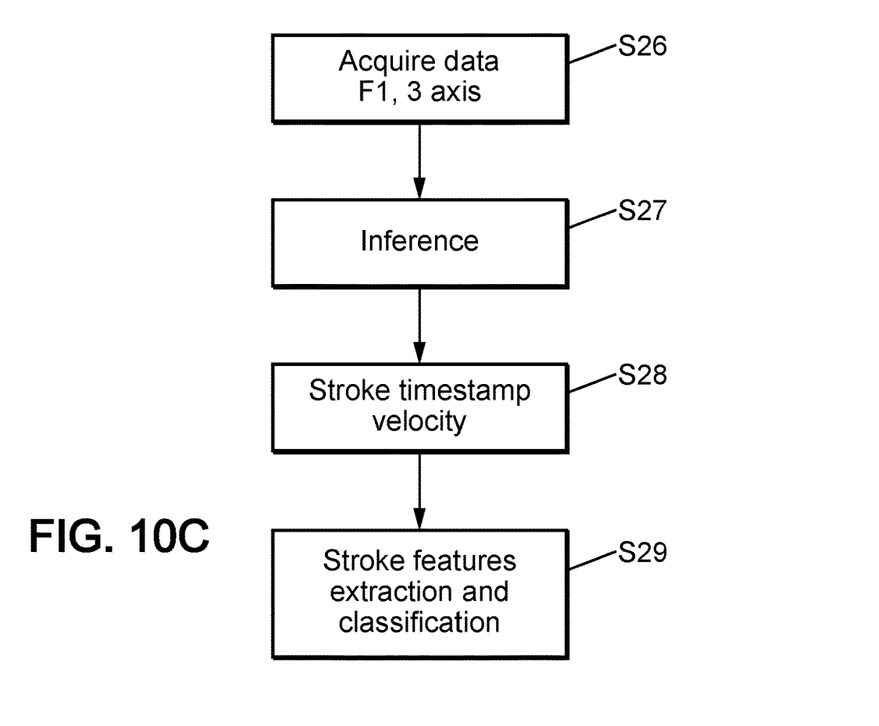

In the embodiment illustrated FIGS. 10A to 10O, the stroke sensor 16 is the motion sensor 7. More specifically, the motion sensor 7 is a three-axis accelerometer.

FIG. 10A illustrates the collect of data used during the training phase of the neural network, which is illustrated FIG. 10B. Finally, FIG. 10C illustrates the inference of the neural network by a user of the handwriting instrument.

To use the motion sensor 7 as the stroke sensor 16, the accelerometer first need to be set such that its sample rate is at least twice superior to the maximum frequency of the vibrations to be detected.

In examples, the accelerometer is highly sensitive. To allow detection of the vibrations by the accelerometer, the accelerometer may be bound to the writing tip 6 of the handwriting instrument 2 by rigid contacts with little damping.

In embodiments, it is possible to enhance the precision of the vibration detection by using a support presenting a rough surface with known spatial frequency.

In FIG. 10A, representing the collect phase, the accelerometer is set with a sample rate F2. While the user is using the handwriting instrument 2, the accelerometer acquires data at step S20. These data can be sent by short-range radio to a recording device at step S21.

In embodiments, during the collect phase, if the handwriting instrument 2 also comprises a three-axis gyroscope as another motion sensor 7, the three-axis gyroscope can also acquire data that are sent to the recording device at step S21.

FIG. 10B illustrates the training phase of the neural network.

At step S22, the data sent to the recording device are provided. The data are analyzed at step S23A to determine the labels (step S23B). For example, the labels comprise the strokes timestamps, detected when vibration is detected in the data, and the stroke velocity. The stroke velocity is advantageously determined using the acceleration data and the high frequencies contained in the vibration.

Step S24 comprises the undersampling of the data. Particularly, during the preceding steps, the frequency of the accelerometer was set to be higher than the one set for the inference phase. Moreover, the vibration analysis was made on the basis of the three-axis accelerometer and the three-axis gyroscope. However, the constant use of the gyroscope leads to high energy consumption.

The undersampling step S24 comprises the degradation of the parameters. Frequency F2 of the accelerometer is reduced to a frequency F1, smaller than F2, and the training is made only according to three-axis detection.

At step S25, the neural network is trained to be able to perform strokes segmentation, as described with reference to FIG. 8, step S2.

FIG. 10C illustrates the inference phase. In this phase, the neural network is trained to detect handwriting problems by means of strokes segmentation.

At step S26, a user is using the handwriting instrument 2 in view of detecting an eventual handwriting problem.

The accelerometer in the handwriting instrument is set to the frequency F1 and advantageously, the data are acquired according to three-axis.

At step S27, the trained neural network is feed with the acquired data. At step S28, the neural network is able to deliver the strokes timestamps and the velocity.

Finally, the neural network is able to perform the intermediate stroke feature extraction and the classification at step S29. Step S29 actually corresponds to steps S4 to S7, already described with reference to FIG. 8.

In embodiments, the neural network can be trained continuously with the data acquired by the user of the handwriting pen 2 after the storage of the neural network.

In embodiments, the neural network can also be trained to detect a wrong ductus of the user. The ductus corresponds to the formation of letter and number.

More specifically, the neural network is able to determine if a sequence of strokes correspond to a letter or a number.

To this end, the neural network can also be fed with a large data base of letters and numbers. Each letters and numbers can be associated with a sequence of strokes. The sequence of strokes can advantageously corresponds to acceleration signals acquired by the accelerometer during the collect phase when forming the letters and numbers.

The labels to be determined by the neural network may be the direction and an order of the sequence of strokes for each letter and number.

In step S5 of FIG. 8, the intermediate features can then also comprise the temporal sequence of strokes and their direction.

In step S7, the neural network is able to determine if the user is forming correctly letters and numbers.

The invention claimed is:

1. A system for detecting handwriting problems comprising:
 a handwriting instrument including a body extending longitudinally between a first end and a second end, the first end having a writing tip which is able to write on a support;
 a detection device distinct from the handwriting instrument, the detection device comprising a body configured to be mounted on the second end of the handwriting instrument and a protuberant tip extending from the body of the detection device and configured to be inserted in the body of the handwriting instrument;
 wherein the detection device comprises:
  two motion sensors configured to acquire data on handwriting of a user when the user is using the handwriting instrument, said two motion sensors being three-axis accelerometers, or one three-axis accelerometer and
  one three-axis gyroscope; and-one calculating unit communicating with the two motion sensors and configured to analyze the data by an artificial intelligence trained to detect whether the user has handwriting problems;
 wherein a first motion sensor of the two motion sensors is provided on the protuberant tip of the detection device that is configured to be inserted in the body of the handwriting instrument and a second motion sensor of the two motion sensors is provided in the body of the detection device;
 wherein the artificial intelligence is at least one neural network configured to be trained by segmentation and classification of strokes to determine timestamps of the strokes on the support based upon motion signals sensed by the two motion sensors.

2. The system according to claim 1, wherein the detection device further includes a short-range radio communication interface configured to communicate raw data acquired by the two motion sensors and a battery.

3. The system according to claim 1, wherein the one three-axis gyroscope comprises a wake-up input suited for receiving a wake-up signal from the one calculating unit when a movement is detected by the one three-axis accelerometer, the one three-axis gyroscope being configured for switching into an active state when the wake-up signal is received.

4. The system according to claim 1, further comprising a pressure sensor, wherein the one calculating unit is configured to receive the data acquired by the pressure sensor.

5. The system according to claim 1, further comprising a stroke sensor configured to acquire stroke data while the user is using the handwriting instrument, the artificial intelligence being further trained with the stroke data to determine the handwriting problems.

6. The system according to claim 5, wherein the stroke sensor is the two motion sensors.

7. The system according to claim 1, wherein the artificial intelligence is further configured to determine when the user is actually using the handwriting instrument on the support and to differentiate data corresponding to an actual use of the handwriting instrument from data acquired while the handwriting instrument is only being held in air.

8. The system according to claim 1, wherein the handwriting instrument is a pen, a pencil a brush or any other element allowing the user to write or draw with it on the support.

9. The system according to claim 1, wherein the artificial intelligence is further configured to transcribe raw data acquired by the two motion sensors into handwriting characters depicted on a mobile device.

10. The system according to claim 1, wherein the support is a non-electronic surface.

11. The system according to claim 1, wherein the one calculating unit comprises a volatile memory to store data acquired by the two motion sensors and a non-volatile memory to store a model enabling the detection of the handwriting problems.

12. The system according to claim 1, wherein the at least one neural network is further configured to acquire data during use of the handwriting instrument and to determine if the user is forming letters and numbers correctly.

* * * * *

UNITED STATES PATENT AND TRADEMARK OFFICE
CERTIFICATE OF CORRECTION

PATENT NO. : 12,379,790 B2
APPLICATION NO. : 17/997904
DATED : August 5, 2025
INVENTOR(S) : Eric Humbert et al.

Page 1 of 1

It is certified that error appears in the above-identified patent and that said Letters Patent is hereby corrected as shown below:

In the Claims

In Column 9, approximately Line 20, in Claim 1, delete "and-one" and insert --and one--.

Signed and Sealed this
Thirtieth Day of September, 2025

John A. Squires
*Director of the United States Patent and Trademark Office*